(12) United States Patent
Deng et al.

(10) Patent No.: US 11,331,409 B2
(45) Date of Patent: May 17, 2022

(54) BIOACTIVE GLASS-POLYMER COMPOSITE BONE SCAFFOLDS

(71) Applicant: Purdue Research Foundation, West Lafayette, IN (US)

(72) Inventors: Meng Deng, West Lafayette, IN (US); Dong Qiu, Biejing (CN); Jessica Lynn Zuponcic, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 57 days.

(21) Appl. No.: 16/179,251

(22) Filed: Nov. 2, 2018

(65) Prior Publication Data

US 2019/0134262 A1 May 9, 2019

Related U.S. Application Data

(60) Provisional application No. 62/581,884, filed on Nov. 6, 2017.

(51) Int. Cl.
| | |
|---|---|
| *A61L 27/18* | (2006.01) |
| *A61L 27/54* | (2006.01) |
| *A61L 27/46* | (2006.01) |
| *A61L 27/58* | (2006.01) |
| *A61L 27/56* | (2006.01) |
| *A61L 27/44* | (2006.01) |
| *A61L 27/12* | (2006.01) |
| *A61L 27/02* | (2006.01) |
| *A61L 27/38* | (2006.01) |
| *A61L 27/10* | (2006.01) |

(52) U.S. Cl.
CPC ............ *A61L 27/18* (2013.01); *A61L 27/025* (2013.01); *A61L 27/12* (2013.01); *A61L 27/3821* (2013.01); *A61L 27/3834* (2013.01); *A61L 27/3847* (2013.01); *A61L 27/446* (2013.01); *A61L 27/46* (2013.01); *A61L 27/54* (2013.01); *A61L 27/56* (2013.01); *A61L 27/58* (2013.01); *A61L 27/10* (2013.01); *A61L 2300/414* (2013.01); *A61L 2300/426* (2013.01); *A61L 2430/02* (2013.01)

(58) Field of Classification Search
None
See application file for complete search history.

(56) References Cited

PUBLICATIONS

Rezwan et al. "Biodegradable and bioactive porous polymer/inorganic composite scaffolds for bone tissue engineering", Biomaterials, 27, 2006, pp. 3413-3431. (Year: 2006).*
Li et al., "Phytic acid derived bioactive CaO—P2O5—SiO2 gel-glasses", J Mater Sci: Mater, Med, 22, 2011, pp. 2685-2691. (Year: 2011).*
Miao et al., "Porous calcium phosphate ceramics modified with PLGA-bioactive glass", Materials Science and Engineering C, 27, 2007, pp. 274-279. (Year: 2007).*
Lu et al., "Three-dimensional, bioactive, biodegradable, polymer-bioactive glass composite scaffolds with improved mechanical properties support collagen synthesis and mineralization of human osteoblast-like cells in vitro", J Biomed Mater Res A, 64(3), 2003, pp. 465-474.. (Year: 2003).*
Wang et al. "Preparation and Characterization of the System SiO2—CaO—P2O5 Bioactive Glasses by Microemulsion Approach", Journal of Wuhan University of Technology-Mater. Sci. Ed., 2013, pp. 1053-1057.. (Year: 2013).*
Lv, Q., et al., "Nano-ceramic Composite Scaffolds for Bioreactor-based Bone Engineering", Clin Orthop Relat Res., 471, pp. 2422-2433, 2013.
Cushnie, E., et al., "Simple Signaling Molecules for Inductive Bone Regenerative Engineering", PLOS, e101627, pp. 11, 2014.
Mauth, A., et al., "Bone morphogenetic proteins in open fractures: past, present, and future", Elsevier, 40, 99, pp. S27-S31, 2009.
Wegman, F., et al., "Gene delivery of bone morphogenetic protein-2 plasmid DNA promotes bone formation in a large animal model", 8, pp. 763-770, 2014.
Narayanan, N., et al., "Polymeric Electrospinning for Musculoskeletal Regenerative Engineering", Regen Eng., Transl., Med., 2, pp. 69-84, 2016.
Brown, J., et al., "Composite scaffolds: Bridging nanofiber and microsphere architectures to improve bioactivity of mechanically competent constructs", Wiley, pp. 1150-1158, 2010.
Gaharwar, A., et al., "Bioactive Silicate Nanoplatelets for Osteogenic Differentiation of Human Mesenchymal Stem Cells", Adv. Mater., 25, pp. 3329-3336, 2013.
Wang, C., et al., "Bioactive Nanoparticle-Gelatin Composite Scaffold with Mechanical Performance Comparable to Cancellous Bones", AMS, 6, pp. 13061-13068, 2014.
Xu, C., et al., "Biocompatibility and osteogenesis of biomimetic Bioglass-Collagen-Phosphatidylserine composite scaffolds for bone tissue engineering", Biomaterials, 32, pp. 1051-1058, 2011.
Hou, G., et al., "In vivo study of a bioactive nanoparticle-gelatin composite scaffold for bone defect repair in rabbits", J Mater Sci, 28, pp. 9, 2017.
Zhang, Q., et al., "Fluorescent PLLA-nanodiamond composites for bone tissue engineering", Biomaterials, 32, pp. 87-94, 2011.
Li, A., et al., "Phytic acid derived bioactive CaO—P2O5—SiO2 gel-glasses", J Mater Sci, 22, pp. 2685-2691, 2011.

* cited by examiner

*Primary Examiner* — Melissa L Fisher
(74) *Attorney, Agent, or Firm* — Lei Fang; Smith Tempel Blaha LLC

(57) ABSTRACT

Disclosed herein is a technology for healing bone defects using bioactive silicate glass (BSG) and a 3D osteomimetic composite porous scaffold containing microspheres comprised of poly(lactide-co-glycolide) (PLGA).

15 Claims, 14 Drawing Sheets

Table 1: EDS analysis of apatite composition on the scaffolds' surfaces after submersion in mSBF for two weeks. Calcium to phosphate ratios are close to that of bone mineral, also known as hydroxyapatite (Ca:P is 1.67). Elements below 1 atomic % not reported.

| Time Point | Scaffold Type | Element | Atomic % | Ratio Ca:P |
|---|---|---|---|---|
| Day 7 | Pure PLGA | O | 46 | |
| | | C | 42.4 | |
| | | Ca | 6.8 | 1.55 |
| | | P | 4.4 | |
| | Composite | O | 47.2 | |
| | | C | 38.2 | |
| | | Ca | 8.6 | 1.59 |
| | | P | 5.4 | |
| Day 14 | Pure PLGA | O | 58.7 | |
| | | Ca | 17.7 | |
| | | P | 11.8 | 1.50 |
| | | C | 10.7 | |
| | Composite | O | 58 | |
| | | Ca | 18.6 | |
| | | P | 12.1 | 1.54 |
| | | C | 9.6 | |

Figure 13

Table 2: Order and concentrations of added reagents in mSBF preparation

| Order | Reagent | Concentration (mM) |
|---|---|---|
| 1 | NaCl | 141 |
| 2 | KCl | 4 |
| 3 | $MgSO_4$ | 0.5 |
| 4 | $MgCl_2$ | 1 |
| 5 | $NaHCO_3$ | 4.2 |
| 6 | 1M HCl | * |
| 7 | $CaCl_2$ | 5 |
| 8 | $KH_2PO_4$ | 2 |
| 9 | Tris | 20 |

*Add ~39 mL per 1L mSBF; pH should be 2.0 +/- 1.0 following this step [35]

Figure 14

BIOACTIVE GLASS-POLYMER COMPOSITE BONE SCAFFOLDS

FIELD OF INVENTION

This disclosure relates to a novel 3D osteomimetic composite with porous scaffold which is developed from composite microspheres comprised of polymers and a novel bioactive silicate glass (BSG). Particularly, optimized composite scaffolds have bone-mimicking structural and mechanical properties and are able to promote osteogenic differentiation and bone regeneration.

BACKGROUND

Annually in the US, there are more than 6.5 million fractures, and 500,000 of the resulting treatments require a bone graft [1, 2]. Bone-grafting procedures are necessary when the wound severity surpasses the bone's ability to auto-repair—known as critical size bone defects. Today's best treatments for critical size defects involve autografts: harvesting a graft from the patient's body, typically from the iliac crest, and transferring it to the wound site [1, 3]. Autografting risks morbidity at the donor site and is size-limited, but autografts retain many ideal bone tissue characteristics—including osteoconductivity, osteoinductivity, and osteogenicity [3]. For procedures requiring more material, grafts from donors or cadavers, known as allografts, can be used. To reduce the risk of rejection and disease transmission, allograft marrow and cellular debris are removed with fluids and detergents, then grafts are typically irradiated and frozen or freeze-dried [1, 4]. Post-processing, allograft osteoinductive and mechanical properties are reduced, and insufficient revascularization or infection contributes to graft failure in 25%-35% of patients [3, 4]. Furthermore, the demand for allografts exceeds supply—necessitating a 3rd treatment strategy involving bone graft substitutes such as bone cements, composite blocks, and gels [1]. 18-20% of procedures require these substitutes [5] and, like allografts, all of these substitutes have little or no osteoinductivity [1].

To augment osteoinductive properties in the allograft or bone-graft substitute, osteoinductive growth factors, known as bone morphogenetic proteins (BMPs), are often added at the surgical site [6, 7]. BMPs were discovered when pieces of decalcified bone, implanted in soft-tissue and bone defect sites of various animal models, prompted completely new bone formation—populated with host osteoprogenitor cells, stem cells, and capillaries [8]. The ability of BMPs to trigger bone formation in soft tissues is potentially very dangerous; excessive application of BMPs at the surgical site may leech into surrounding soft tissue and form bone ectopically [6, 7, 9]. Despite the risks, BMPs are often applied in supraphysiological concentrations to sustain their effects—a result of the protein's short half-life [10, 11]. An additional burden on BMP usage is cost—about $5,000 US per dose [9]. These drawbacks and clinical challenges have inspired decades of research to develop bone graft substitutes that can trigger new bone formation, exhibit bioactivity (bond to surrounding bone in the wound site), allow host cell infiltration and migration (osteoconductivity), provide suitable mechanical and load-bearing properties, exhibit biocompatibility, degrade to allow host tissue replacement, and be cost-effective [3, 12]. Thus, there is an unmet need to develop suitable alternatives of traditional bone grafts and BMP usages.

SUMMARY OF THE INVENTION

This disclosure provides a three dimensional osteomimetic composite porous scaffold comprising a polymer and a bioactive silicate glass (BSG) derived from phytic acid, tetraethyl orthosilicate (TEOS) and/or calcium nitrate, wherein the polymer may be any one or a combination of biocompatible polymers—including poly(glycolic acid) (PGA), poly(lactic acid) (PLA), poly(lactic-co-glycolic acid) (PLGA), polycaprolactone (PCL), poly(propylene fumarate), collagen, polyphosphazenes, polyanhydrides, poly(amino acids), polyhydroxyalkanoates, polyethylene glycol (PEG), polydioxanone (PDO), polysaccharides (e.g. hyaluronic acid, chitosan, dextran, chondroitin sulfate, alginate, and cellulose), and others. The weight of BSG is about 2% to about 40% of the polymer weight (i.e. BSG comprises about 2%-28.6% by weight of the composite material).

In some preferred embodiment, the bioactive glass comprises about 10% of the polymer weight.

In some preferred embodiment the bioactive glass comprises about 9.1% weight of the composite scaffold material.

In some preferred embodiment the BSG is a ternary combination of SiO2, P2O5 and CaO.

In some preferred embodiment the bioactive glass comprises about 6-80 mol % SiO2.

In some preferred embodiment the bioactive glass comprises about 0-70 mol % P2O5.

In some preferred embodiment the bioactive glass comprises about 15-85 mol % CaO.

In some preferred embodiment the bioactive glass comprising about 10.8 mol % $P_2O_5$, about 54.2 mol % $SiO_2$, and about 35 mol % CaO.

In some preferred embodiment the composite may exist in several forms including microspheres, nanospheres, fibers, monoliths, films, etc.

This disclosure further provides a method of fabricating a composite scaffold material comprising a polymer and a bioactive glass, comprising the steps of:
a. Dissolving any polymer selected from the group consisting of poly(glycolic acid) (PGA), poly(lactic acid) (PLA), poly(lactic-co-glycolic acid) (PLGA), polycaprolactone (PCL), poly(propylene fumarate), collagen, polyphosphazenes, polyanhydrides, poly(amino acids), polyhydroxyalkanoates, polyethylene glycol (PEG), polydioxanone (PDO), polysaccharides (e.g. hyaluronic acid, chitosan, dextran, chondroitin sulfate, alginate, and cellulose), and others in a solvent to form a polymer solution;
b. Incorporating bioactive glass powder derived from phytic acid, tetraethyl orthosilicate or calcium nitrate into the polymer solution, wherein the bioactive glass powder comprises an amount less than about 40% of the polymer weight (i.e. glass comprises less than about 28.6 wt % of the composite), down to about 2% of the polymer weight (2.0 wt % of the composite); and
c. Allowing the solvent to evaporate from the solution to form the composite scaffold.

In some embodiment, in the aforementioned method the bioactive glass powder is incorporated via any one or a combination of methods including sonication and vortex mixing.

In some embodiment, in the aforementioned method the solvent is organic or inorganic including but limited to one or a combination of solvents such as dichloromethane, methanol, ethanol, chloroform, acetone, toluene, acetic acid, isopropanol, water, etc.

In some embodiment, in the aforementioned method the composite solution solvent evaporation can take place in several ways—including but not limited to droplets in an emulsion and inside molds of various shapes.

This disclosure further provides a porous biocompatible scaffold consisting of aforementioned composite comprising of a polymer and a bioactive glass derived from phytic acid, tetraethyl orthosilicate (TEOS), and/or calcium nitrate.

In some embodiment the aforementioned scaffold is derived by one or a combination of methods including solvent casting and particulate leaching, phase separation and freeze drying, solution spinning, microsphere sintering, hydrogel formation, and rapid prototyping technologies.

This disclosure further provides a method of effecting bone repair comprising contacting the area affected by a bone defect with the aforementioned scaffold material.

In some embodiment the aforementioned composite scaffold material further comprises a bioactive agent selected from the group consisting of: bone morphogenic proteins (BMPs), vascular endothelial growth factor (VEGF), connective tissue growth factor (CTGF), osteoprotegerin, growth differentiation factors (GDFs), cartilage-derived morphogenic proteins (CDMPs), LIM mineralization proteins (LMPs), transforming growth factor β (TGFβ), antibiotics, immunosuppressive agents, and combinations thereof.

In some embodiment the aforementioned scaffold further contains host-derived cells including, but not limited to, mesenchymal stem cells, osteoprogenitors, pre-osteoblasts, osteoblasts, or a combination of these cells.

These and other features, aspects and advantages of the present invention will become better understood with reference to the following figures, associated descriptions and claims.

Figure 1:
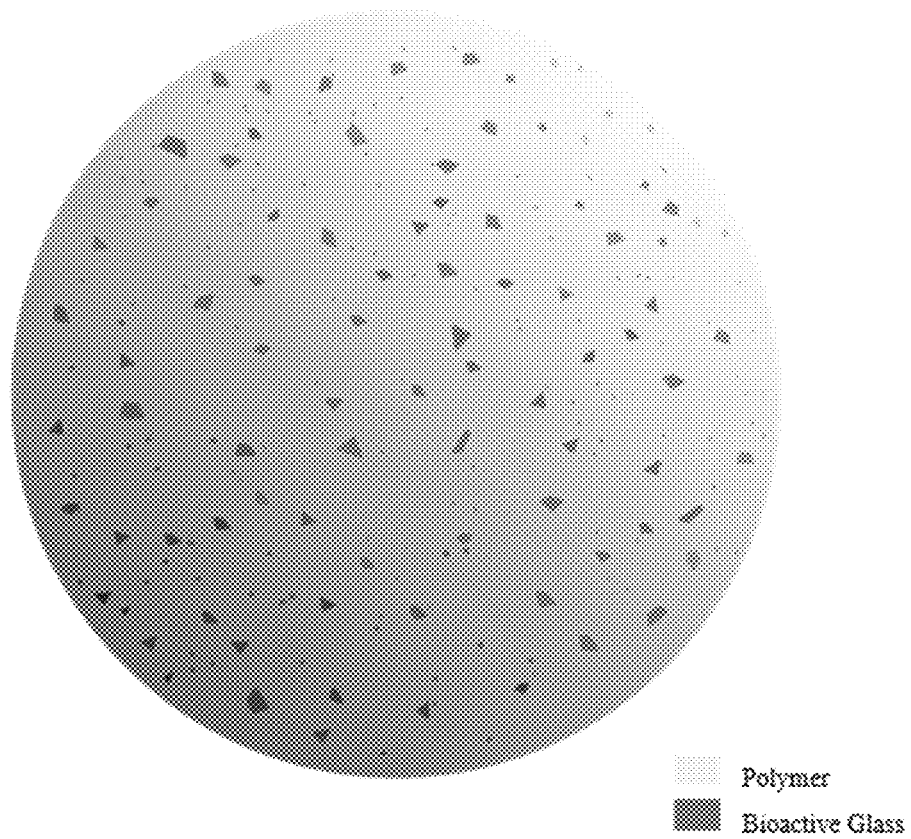
FIG. 1: Example sphere of composite material containing a polymer and the novel bioactive silicate glass. The polymer may be any one or a combination of biocompatible polymers—including poly(glycolic acid) (PGA), poly(lactic acid) (PLA), poly(lactic-co-glycolic acid) (PLGA), polycaprolactone (PCL), poly(propylene fumarate), collagen, polyphosphazenes, polyanhydrides, poly(amino acids), polyhydroxyalkanoates, polyethylene glycol (PEG), polydioxanone (PDO), polysaccharides (e.g. hyaluronic acid, chitosan, dextran, chondroitin sulfate, alginate, and cellulose), and others. The weight of BSG is about 2% to about 40% of the polymer weight (i.e. about 2%-28.6 wt % of the composite).
Figures 2A, 2B, 2C, 2D, 2E:
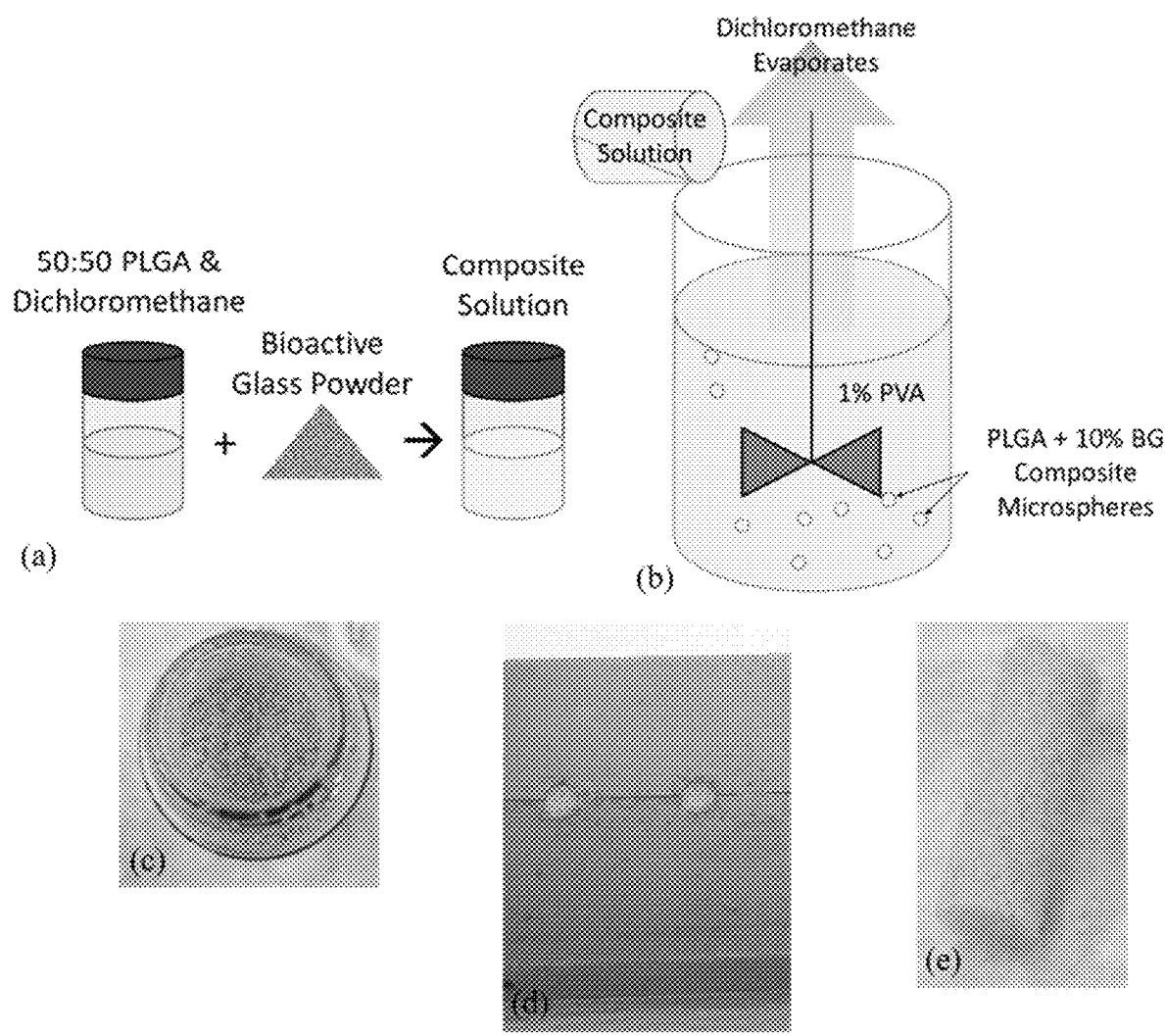
FIGS. 2(a)-2(e): Process diagram of composite scaffold manufacturing. (a) 8% (w/v) 5050 PLGA was dissolved in dichloromethane. Bioactive silicate glass (BSG) powder was added to the polymer solution (10% by weight of the polymer) and placed in a bath sonicator for 30 minutes. (b) Microspheres were formed using an emulsion/solvent evaporation technique [11]; the BSG dispersion was poured into a 1% PVA solution, and the mixture was stirred at 400 rpm until complete solvent evaporation. The resulting composite microspheres were rinsed and dried. (c) Microspheres were sieved to obtain a desired diameter range of 250-500 μm. Before sintering, the microspheres were dried in a lyophilizer overnight. (d) Microspheres were packed into a cylindrical mold (0.5 cm diameter; 1.5 cm long), and heated in an oven at 90° C. for 2 hours. (e) Once the mold cooled to room temperature, it was opened and the scaffolds were removed. Inclusion of BSG in the composite imparted opaqueness to the scaffold—compared to pure PLGA scaffolds which were translucent.
Figures 3A, 3B, 3C, 3D, 3E:
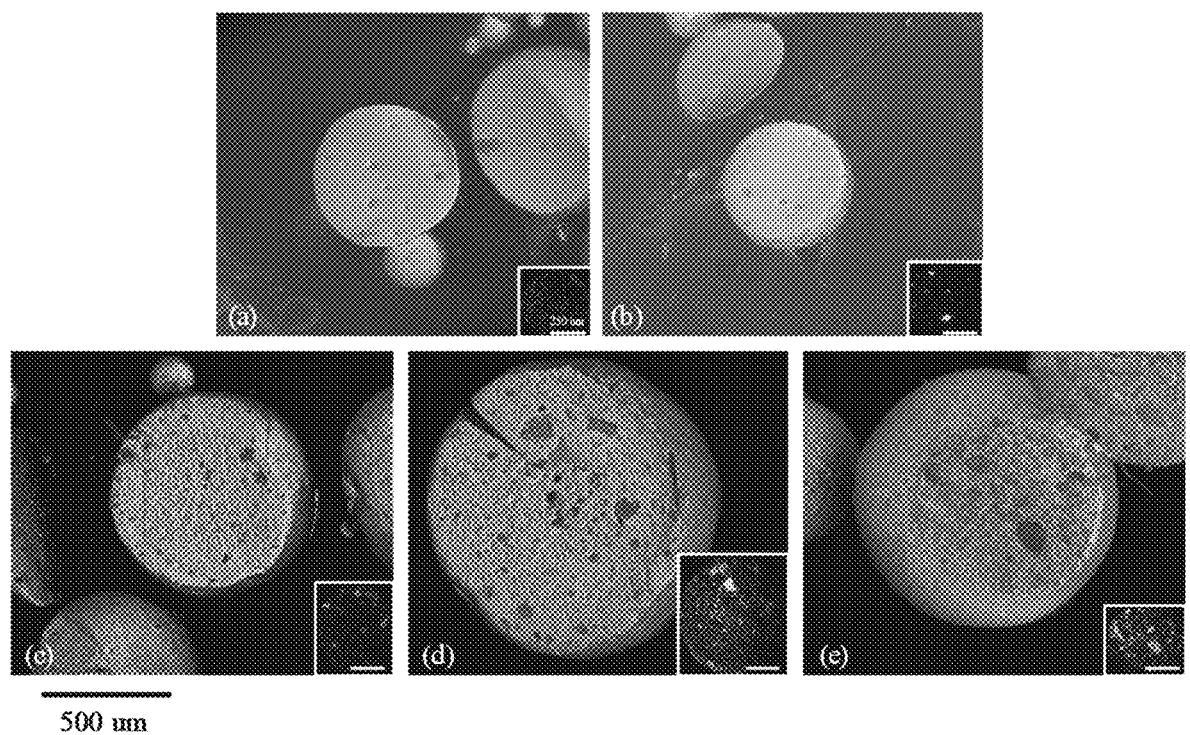
FIGS. 3(a)-3(e): SEM micrographs of composite microsphere interiors containing different levels of BSG. Microspheres contain (a) 2%, (b) 5%, (c) 10%, (d) 20%, and (e) 40% BSG by polymer weight. Insets: EDS mapping of silicon in composite microsphere interiors indicates presence and dispersion of the ceramic. Large agglomerations (>about 125 μm) began to form above 10% BSG content by polymer weight. Inset scale bar represents 250 μm.

Beneath (a)-(d) are corresponding enlarged SEM images of the mineralized scaffold surfaces: (e) pure PLGA at day 7. (f) composite at day 7. (g) pure PLGA at day 14, and (h) composite at day 14. Morphology of the mineral layer appeared as randomly oriented plate-like structures.

FIGS. 7(a)-7(d): EDS analysis of the scaffolds' surfaces confirmed presence of deposited calcium and phosphorous—as well as remaining silicon from the BSG. Scale bar represents 500 μm.

FIGS. 8(a)-8(h): Confocal z-stack images of hMSCs on scaffolds. A live/dead fluorescent assay was performed on days 1 and 3 to assess cell viability—with green fluorescence occurring on live cells and red fluorescence on dead cells. Both scaffold types supported cell viability. (e-h) Hoechst and TRITC staining at days 14 and 21 illustrated cell morphology and scaffold coverage. Cell nuclei fluoresced blue; cell actin fluoresced red. Day 1 z-stack micrographs spanned 100 μm depth. Days 3, 14, and 21 z-stack micrographs spanned 300 μm depth.

FIGS. 9(a)-9(d): SEM micrographs of cells and extracellular matrix deposition on pure PLGA (a,c) and composite (b,d) scaffolds at day 14 (a,b) and day 21 (c,d). By day 14, cells had covered the topmost layer of the scaffolds—evidenced by cell bridging between adjacent microspheres and changes in scaffold topography. Surfaces and bond regions were covered by cellular layers and ECM components—creating rough, irregular surface features and concealing bond areas. White arrows indicate where these features are apparent.

Figures 10A, 10B, 10C:
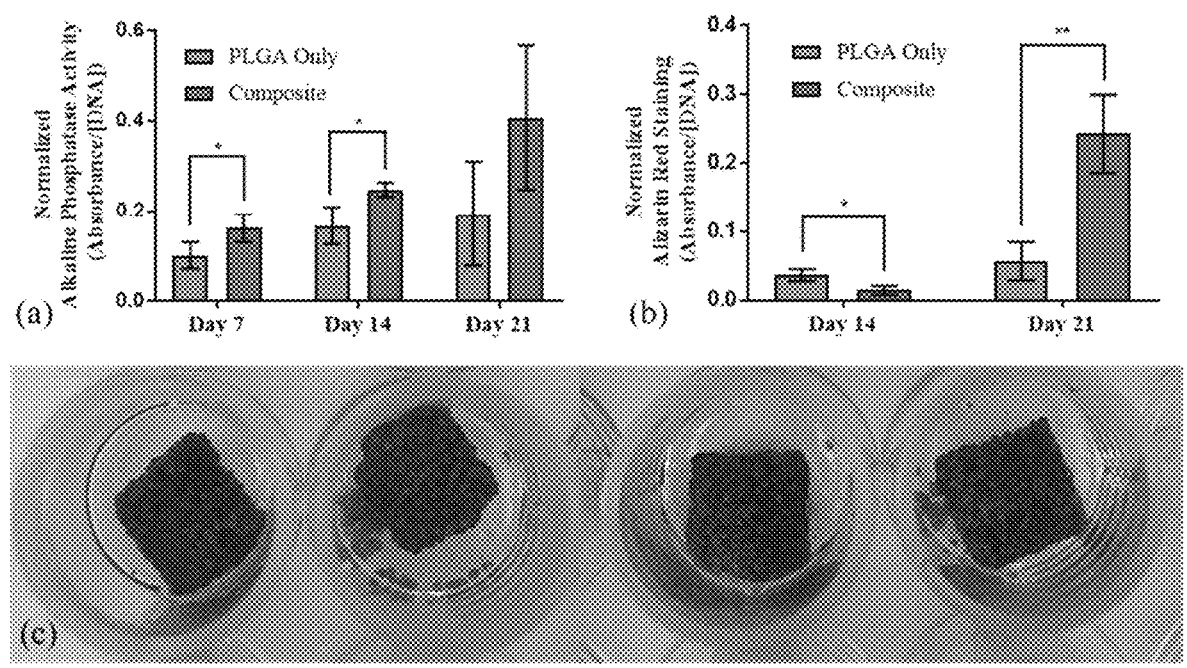
Figures 11A, 11B, 11C, 11D:
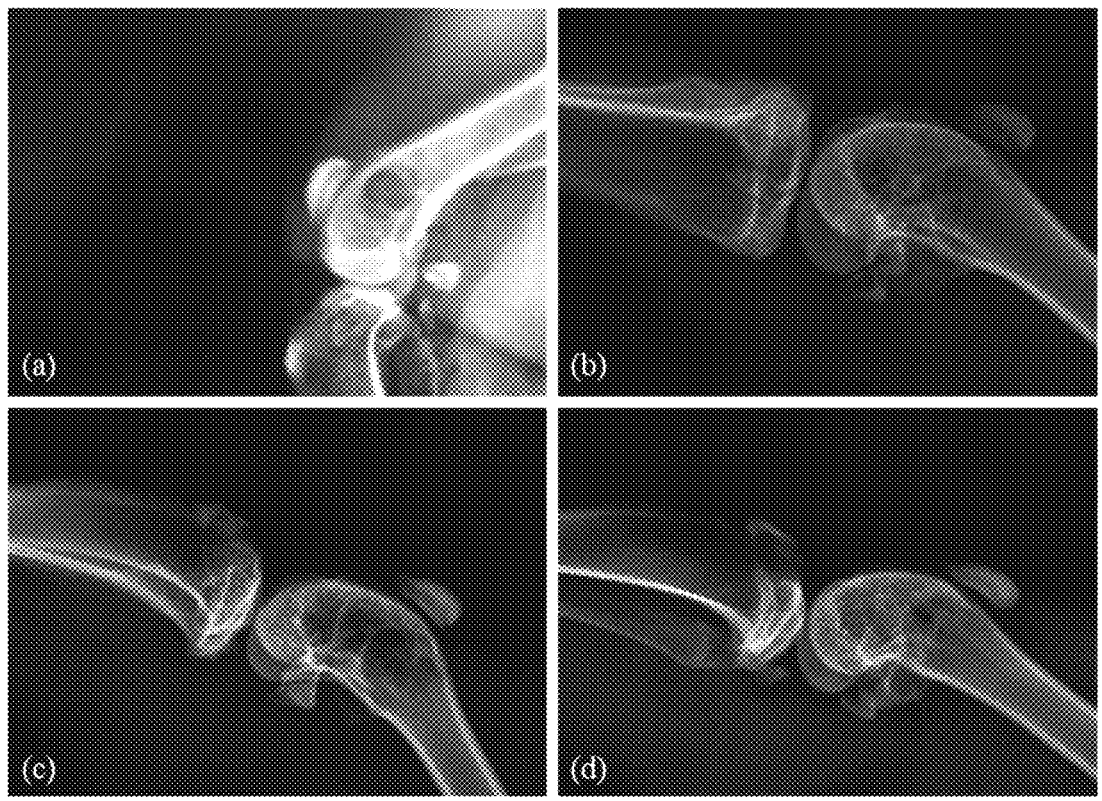
Figures 12A, 12B, 12C, 12D, 12E, 12F:
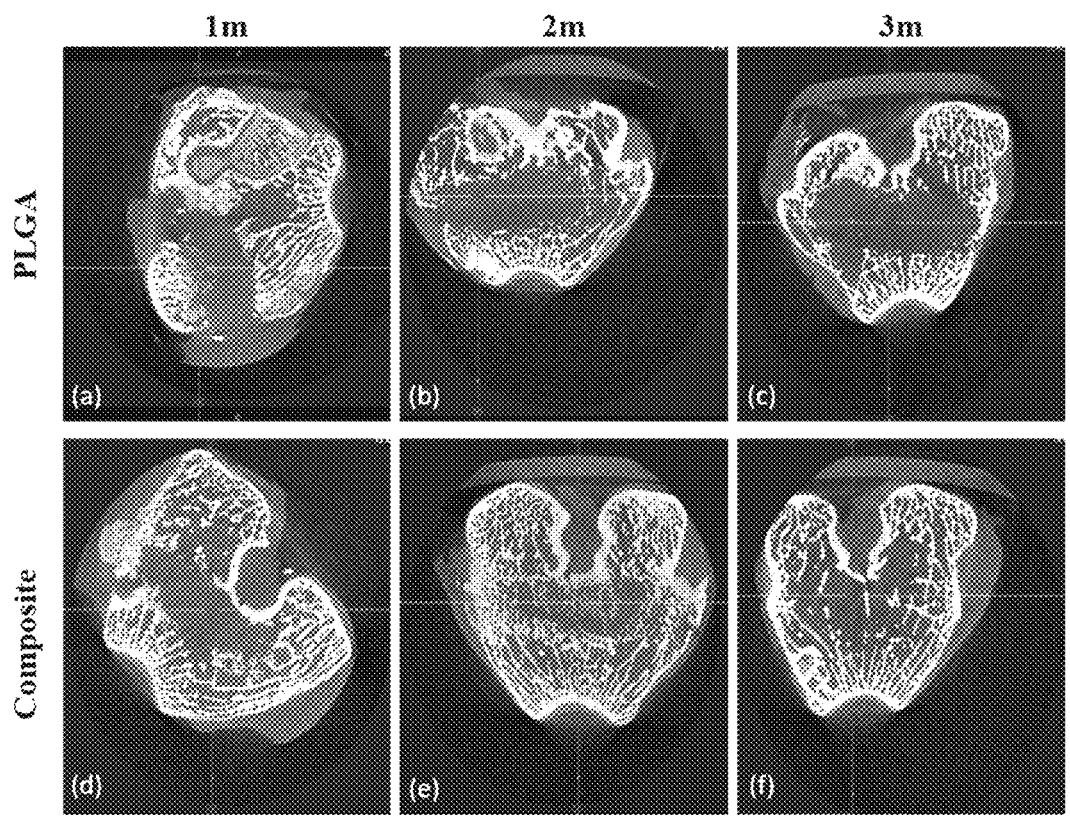

FIGS. 10(a)-10(c): Alkaline phosphatase (ALP) activity, an early marker of osteogenic differentiation, was assayed at days 7, 14 and 21. Greater ALP activity was seen on composite scaffolds at days 7 and 14. Error bars represent standard deviation. *p-value<0.05 (b) Quantification of cell mineralization on scaffolds by Alizarin Red staining at days 14 and 21. Error bars represent standard deviation. *p-value<0.05 **p-value<0.01 (c) Optical micrographs presenting intense Alizarin Red stain of cell-seeded composite scaffolds after 21 days of hMSC culture.

FIGS. 11(a)-11(d): X-ray radiographs of rabbit femoral defect sites after three months. (a) Control defect site, containing no scaffold, after one month. (b) Control defect site after three months. (c) Pure PLGA scaffold treatment after three months. (d) Composite scaffold treatment after three months. The composite scaffold treatment demonstrated the greatest radiopacity in the defect site after three months—evidencing greater bone formation in the defect site compared to pure PLGA or control.

FIGS. 12(a)-12(f): Pure PLGA and composite scaffolds were implanted in rabbit femoral defects for three months. Micro-CT scans evaluated bone ingrowth and formation at the defect sites following implantation of (a-c) PLGA scaffolds and (d-f) composite scaffolds at various time points. The defect site treated with a composite scaffold showed bone ingrowth after two months. Trabeculae-like bone structures were formed within the defect site after three months of composite scaffold implantation.

FIG. 13 represents Table 1: EDS analysis of apatite composition on the scaffolds' surfaces after submission in mSBF for two weeks.

FIG. 14 represents Table 2: Order and concentration of added reagents in mSBF preparation.

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

Unless defined otherwise, the scientific and technology nomenclatures have the same meaning as commonly understood by a person in the ordinary skill in the art pertaining to this disclosure.

As used herein, "sintering" is the process of compacting and forming a solid mass of material by heat or pressure without melting it to the point of liquefaction. Sintering happens naturally in mineral deposits or as a manufacturing process used with metals, ceramics, plastics, and other materials.

A broken bone unable to heal on its own is considered to have experienced a critical size defect. The use of one's own bone tissue is currently the best available option, except it requires two surgeries, the material available is limited, and there is a risk of donor-site morbidity. The other option is to use bone tissue from a donor or a cadaver; these offer more material, but there is a risk of disease transmission, reduction of osteoinductive properties, and lack of osteogenic cellular components. In addition, bone morphogenetic proteins (BMPs) are sometimes used to improve osteoinductivity, but these proteins have a short half-life and must be added in supraphysiological doses. There is a risk of ectopic bone formation when using BMPs. There is a need for a safer, more beneficial approach to bone regeneration.

Disclosed herein is composition and method for healing bone defects using bioactive silicate glass (BSG) and a 3D osteomimetic composite porous scaffold containing microspheres comprised of poly(lactide-co-glycolide) (PLGA). Unlike other bioactive glasses which increase local pH, this BSG product demonstrates fast dissolution and ion release without impacting local pH; in addition, this BSG also has higher phosphorous content, and high calcium content, compared to other commercially available BSGs. The beneficial mechanical properties of PLGA are combined with the bioactivity of the BSG, introducing the possibility of a composite replacing autografts, allografts, and BMPs.

Directing osteogenic differentiation of mesenchymal stem cells (MSCs) represents a promising strategy for bone repair. Current paradigms in directing MSC osteogenic differentiation using growth factors are plagued by safety and efficacy concerns. For example, the application of exogenous bone morphogenetic proteins (BMPs) has been hindered by concerns over supraphysiological dosage requirements and undesirable immunological reactions. Our previous studies have demonstrated the osteoinductive potential of calcium and phosphate ions to trigger endogenous MSC-based BMP-2 production. Thus, bioactive glass offers an attractive approach for inducing osteogenic differentiation leading to bone formation due to its ion release capacity. The desire is to develop osteomimetic and osteoinductive composite scaffolds to promote bone regeneration.

Besides loading a substrate with BMPs, several other strategies have been developed to improve osteoinductivity. To avoid supraphysiological dosing, cells can be transfected to express BMP, or other osteogenic pathway signals, in situ [13, 14]. More clinically relevant options, avoiding genetic modification, involve topographical cues and ion induction strategies. Cells, including osteoprogenitor and human mesenchymal stem cells (hMSCs), use focal adhesion proteins to attach to the surrounding environment, transmit forces across the cytoskeleton, and regulate gene expression via the mechanotransduction pathway [15]. Topographical features, such as nanopits or nanofibers, have demonstrated potential to promote osteogenic differentiation [16, 17]. Finally, several ceramic materials, including certain bioactive glasses, hydroxyapatite, tricalcium phosphate, and biphasic calcium phosphate, have demonstrated osteoinductive properties [2, 5, 11, 18-21]. Some researchers have attributed these properties only to the topography of the ceramics following their reaction with body fluid. Submersion of these materials in body fluid results in the deposition of a calcium phosphate apatite layer which could influence the cells' mechanotransduction pathways [22]. Alternatively, there is some evidence that calcium and phosphate ions, which are released as these materials degrade, are simple signaling molecules—directly interacting with cells to stimulate osteogenic differentiation [5, 19, 22].

An additional benefit of some of these ceramic materials is their ability to form a physical bond with surrounding bone in the wound site—known as bioactivity. This property is attributed to many organic and inorganic materials such as collagen, demineralized bone matrix, calcium carbonate, calcium sulfate—as well as the aforementioned bioactive glasses [23, 24]. Unfortunately, bioactive glasses are brittle; they do not have the mechanical integrity to function as graft substitutes on their own. They are frequently made into composites with biodegradable, biocompatible polymers—such as PLGA, polyphosphazenes, chitosan, or gelatin—which provide more suitable mechanical properties while releasing the glass over time [17, 25-28]. This combination resembles that of bone which is also a composite of organic and inorganic components—collagen and hydroxyapatite [29].

In this study, a novel 3D osteomimetic composite porous scaffold was developed by sintering of composite microspheres comprised of poly(lactide-co-glycolide) (PLGA) and a novel bioactive silicate glass (BSG). This combination synergistically merged the benefits of mechanical properties of PLGA with the bioactivity of the BSG. Composite scaffolds were optimized to obtain bone-mimicking structural and mechanical properties by controlling fabrication parameters including BSG weight percentage and sintering conditions. The optimized composite scaffold exhibited compressive properties in the mid-range of trabecular bone. Furthermore, the composite scaffolds supported adhesion and growth of human MSCs during a 3-week cell culture. Interestingly, the composite scaffolds significantly increased the alkaline phosphatase activity of the cells leading to enhanced mineralization as compared to control PLGA scaffolds. These experiments supported the promise of developing next generation osteoinductive composite scaffolds for healing large bone defects.

Composite scaffolds were fabricated from 50:50 PLGA and 10% BSG. The goal of this study was to determine whether these composite scaffolds would have greater effects on hMSC osteogenic differentiation compared to pure PLGA scaffolds. Additionally, it was hypothesized that the PLGA component would provide suitable mechanical properties for bone tissue engineering—which cannot be obtained from using BSG alone. Compression testing verified the scaffolds exhibited an elastic modulus in the range of trabecular bone, and they mimicked trabecular bone's triphasic compression behavior. When designed scaffolds for tissue regenerative engineering, imitation of the native tissue's mechanical properties is key to providing cellular environmental cues—triggering cells to form appropriate ECM, signaling, and attachment proteins.

Furthermore, the composite scaffolds exhibited higher levels of ALP activity and ECM mineralization than pure PLGA scaffolds. This provided evidence of BSG contribution towards osteoinduction. Mineralization is also favorable for scaffold integration with surrounding bone tissue.

2. Materials and Methods
2.1 Materials

Scaffolds were made from a composite of 50:50 PLGA and a novel bioactive silicate glass (BSG). The PLGA (product 5050 DLG 7E, with Mw=106 kDa, Mn=64 kDa, and $T_g$=47.9° C.) was obtained from Lakeshore Biomaterials (Evonik Industries). The BSG was fabricated by Dr. Dong Qiu's lab at the Beijing National Laboratory for Molecular Sciences. It is comprised of 10.8 mol % $P_2O_5$, 54.2 mol % $SiO_2$, and 35 mol % CaO. Phosphate buffered saline (PBS) and growth medium components, low-glucose DMEM, fetal bovine serum (FBS), L-glutamine, and penicillin/streptomycin (P/S), were obtained from Life Technologies (Thermo Fisher Scientific). Osteogenic medium components—dexamethasone, β-glycerophosphate, and L-ascorbic acid 2-phosphate—were obtained from Sigma-Aldrich. Human mesenchymal stem cells (hMSCs) were purchased from Lonza.

2.2 Fabrication and Sintering of Composite Microspheres

The amount of BSG in the composite was optimized by evaluating the dispersion of the BSG powder at different levels inside the microspheres with SEM and EDS microscopy (Quanta 3D FEG from FEI). BSG powder was added as a weight percentage of the PLGA; levels included 2%, 5%, 10%, 20%, and 40% BSG. Microspheres were formed using the emulsion/solvent evaporation technique outlined in Deng at al [11]. First, 8% (w/v) PLGA was dissolved in dichloromethane. BSG powder was added to the polymer solution and placed in a bath sonicator for 30 minutes. The final dispersion was poured into a 1% PVA solution, and the mixture was stirred until the solvent evaporated. The resulting composite microspheres were rinsed and dried, then sieved to obtain a diameter range within 250-500 μm. The microspheres were lyophilized overnight, packed into a cylindrical mold (0.5 cm diameter; 1.5 cm long), and heated in an oven at 90° C. for 2 hours. Pure PLGA scaffolds, without any added BSG, were fabricated as a comparison against the composite.

2.3 Characterization of the Scaffold
2.3.1 Mechanical Testing

Compression testing was performed on an MTS Criterion Model 43 as described in Jiang et al. [27]. Cylindrical scaffolds were cut to 1 cm in length—achieving a 2:1 length to diameter ratio. Scaffolds were compressed at a cross head speed of 5 mm/min at atmospheric conditions. The elastic modulus was averaged from n=7 compressions.

2.3.2 Porosity

Initial scaffold imaging was done in a Skyscan 1172 (Bruker) micro computed tomography (μCT) scanner. The bioactive glass material had a greater radiopacity than PLGA; thresholding was used to locate the BSG material within the composite.

Further porosity analysis was done on a Quantum GX μCT (PerkinElmer). Scaffolds were scanned at 90 kV and 88 μA—using a 36 mm field of view (FOV) for 14 min (high-resolution scan settings). From this, 12.23 $mm^3$ sub-volumes of the scaffolds were reconstructed with a voxel size of 4.5 m. A median filter was applied to each scan using a kernel size=5. Scaffold material and air were differentiated using thresholding tools, and the volumes of each were calculated in the region of interest tool.

2.3.3 Biomimetic Studies

Modified simulated body fluid (mSBF), containing twice the calcium (5 mM) and phosphate (2 mM) concentrations of body fluid, was prepared per Kokubo et al. [30] (Table 2). Scaffolds were submerged in mSBF and incubated at 37° C. for a period of two weeks. The mSBF was changed daily. Upon retrieval at days 7 and 14, scaffolds were rinsed three times in deionized water and dried in a desiccator. Low-vacuum EDS, without sample coating, was utilized to measure the composition of the mineral layer on the scaffolds.

High vacuum SEM of platinum-coated samples captured the mineral layer morphology. Samples were coated for 60 seconds with a 208HR sputter coater (Cressington) set to 40 mA. The sample stage was tilted 45 degrees and rotated during the coating deposition to cover the entirety of the samples' surfaces. Mineralized surfaces of the composite scaffolds were compared to those of pure PLGA.

2.4 In Vitro Studies
2.4.1 hMSC Cell Culture

Growth medium was made with 88% low glucose DMEM, 10% FBS, 1% L-glutamine, and 1% penicillin/streptomycin. HMSC were expanded in growth medium until passage four. Prior to seeding, scaffolds were sterilized by immersion in 70% ethanol for 10 minutes, rinsing in sterile water, and exposure to UV light for at least 30 min on all surfaces [27]. 50,000 hMSCs were seeded per scaffold in a 48-well plate, then cultured in osteogenic medium for three weeks. Osteogenic medium was made by adding 10 nM dexamethasone, 20 mM β-glycerophosphate, and 50 μM L-ascorbic acid 2-phosphate to growth medium. During both cell expansion and scaffold maintenance, the incubator was kept at 37° C. and 5% $CO_2$.

2.4.2 hMSC Viability

At days 1 and 3, live-dead (EthD-1 and Calcein AM) fluorescent assays were performed on a Nikon A1R MP confocal microscope. At each time point, the medium was removed from the wells and rinsed with PBS two times. EthD-1 and Calcein AM were combined in PBS to achieve 4 μM and 2 μM concentrations respectively. A 5:2 volumetric ratio of PBS and the dye mix was added to each well and incubated for 30 minutes at room temperature; scaffolds were transferred to a glass-bottom dish and covered with anti-fade medium before imaging at 0.8 μM depth increments. Live and dead cells fluoresced green and red respectively. Control scaffolds, without cells, were examined to determine the presence of background fluorescence from the scaffold material.

2.4.3 hMSC Morphology and Scaffold Coverage

At two and three-week time points, scaffold cell coverage & hMSC morphology were evaluated with nuclei and actin cytoskeleton staining. Cell-seeded scaffolds were fixed using 4% paraformaldehyde. Following fixation and rinsing, cells were permeabilized with 0.1% TritonX-100 solution. Blocking solution was applied to prevent non-specific staining, and the scaffolds were submerged in a dye mix containing Hoechst 33342 (Life Technologies, Thermo Fisher Scientific) and TRITC-conjugated phalloidin (Millipore). The scaffolds were washed, transferred to a glass-bottom dish, and covered with anti-fade medium before z-stack imaging at 0.8 μM increments.

ECM deposition and cell-covered scaffold topography were also examined at two and three-week times points with SEM. Cell-seeded scaffolds were fixed with 4% paraformaldehyde before dehydration in a sequence of ethanol dilutions—50%, 70%, 80%, 90%, 95%, then 100% by volume. The scaffolds were coated in platinum, as described earlier, before examination under SEM.

2.4.4 Proliferation

Proliferation was quantified using the Quant-iT PicoGreen dsDNA Assay Kit from Invitrogen (Thermo Fisher Scientific). Both composite and pure PLGA scaffolds (n=4) were cultured as described earlier—along with acellular scaffolds as a control. At each time point, scaffolds were washed with PBS twice, moved to new wells, covered in 1% Triton X-100, and frozen at −80° C. After three freeze/thaw cycles, the lysed cell solution in each well was measured for DNA concentration. Briefly, cell lysate was diluted in TE buffer and combined with the Pico Green fluorescent reagent. After incubating for five minutes at room temperature, the samples were plated and read in a Synergy H1 microplate reader (BioTek Instruments) set for excitation at 485 nm with a 535 nm emission. Fluorescence from acellular scaffolds was subtracted from sample fluorescence to eliminate background fluorescence. A standard curve was generated, from which sample DNA concentration could be derived, using a range of known DNA concentrations.

2.4.4 Osteogenic Differentiation and Mineralization

A colorimetric alkaline phosphatase (ALP) activity assay (Bio-Rad Laboratories) was used as a metric for the extent of hMSC osteogenic differentiation. Cell lysate from the same wells as the Quant-iT PicoGreen assay (n=4 with an acellular control) was sampled for this assay. P-nitrophenyl-phosphate (pNPP) tablets were dissolved in diethanolamine buffer and added to the cell lysates from each scaffold. Incubation at 37° C. for 30 minutes allowed the ALP enzyme to dephosphorylate the pNPP reagent—resulting in a yellow color change. The dephosphorylating reaction was stopped using 0.4N NaOH, and the samples were subsequently evaluated in the Synergy H1 microplate reader (BioTek Instruments) for absorbance at 405 nm. Baseline absorbance values, from acellular controls, were subtracted from the samples' absorbance values. These corrected absorbance values were normalized to DNA concentration from the same well. Normalized absorbance was compared between pure PLGA and composite scaffolds—where greater absorbance is associated with greater ALP activity.

Alizarin red staining of calcium on cell-deposited mineralization also monitored osteogenic differentiation at days 14 and 21. Cells were seeded onto composite and pure PLGA scaffolds (n=4 with an acellular control) as described previously. At each time point, the cultured scaffolds were rinsed with water and moved to a clean well before fixation in 70% ethanol for 1 hour at 4° C. Samples were rinsed and covered in a 40 mM alizarin red (pH=4.23) for 10 minutes. Dye-covered scaffolds were washed five times, and the remaining dye was dissolved overnight in 10% w/v cetylpyridinium chloride (CPC) for 24 hours. The concentration of the dissolved alizarin red dye was quantified in the Synergy H1 microplate reader (BioTek Instruments)—measuring absorbance at 562 nm. Baseline absorbance values, from acellular controls, were subtracted from the samples' absorbance values, then averaged and normalized to DNA concentration.

2.5 In Vivo Studies

Rabbit femoral defects were 5 mm in diameter and 2 cm in depth. Pure PLGA and composite scaffolds were implanted according to the procedure in Hou et al.—using a non-scaffold defect site as a control [31]. Rabbits were studied over a three month period.

2.6 Statistical Analysis

All quantitative data were reported as mean±standard deviation. Statistical analysis was performed in Minitab software (Minitab Inc.) to determine the existence of outliers and statistical differences. Outliers were explored using the Dixon's Q test and interquartile range (IQR) methods; all outliers are identified alongside the results. Differences between two means were determined using a two-sided t-test—assuming unequal sample variances.

Example 1. Optimization of Bioactive Silicate Glass Content

Microspheres containing various amounts of BSG were bisected and evaluated under SEM & EDS for BSG homogeneity (FIGS. 3(a)-3(e)). Agglomerations of BSG within the PLGA were apparent—especially at the highest concentrations. Agglomeration of the dispersed phase is common in the creation of composites, and it is attributed to charge differences between the two materials. Prior studies have shown hydroxyapatite dispersed in PLA and PLGA to form agglomerations—where hydroxyapatite is hydrophilic in comparison to the polymer [32, 33]. Materials that are hydrophobic in comparison to the polymer, such as diamond particles, will aggregate as well [34]. In this study, agglomerations were apparent at high concentrations of BSG (above 10%) where >125 um diameter agglomerations of BSG can be seen within the microsphere (FIGS. 3(a)-3(e) insets). Agglomerations contribute to variable ion release and BSG content, and they interfere with sphere-to-sphere bond formation. When present near the surface of a microsphere, an agglomeration can occupy the sphere-to-sphere bond area—preventing polymer in that area from participating in a bond (FIGS. 4(a)-4(e)). 10% BSG was the highest concentration of ceramic that could be added before large agglomerations formed.

Figures 4A, 4B, 4C, 4D, 4E:
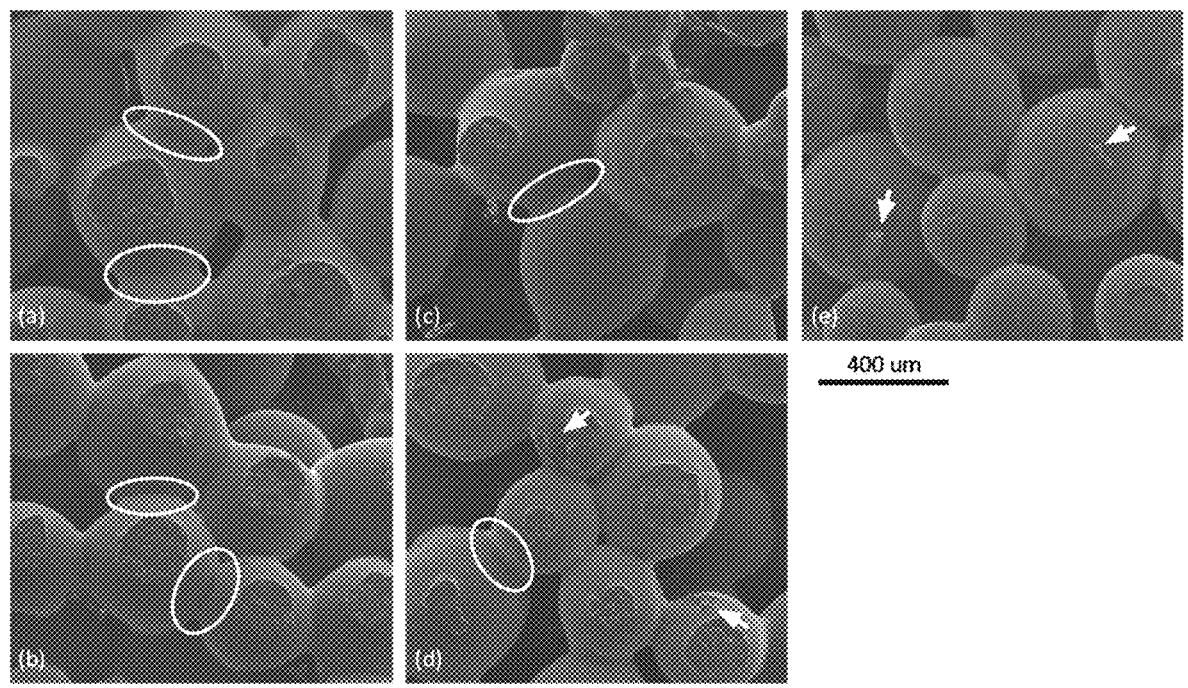
FIGS. 4(a)-4(e): SEM micrographs of sintered microspheres containing different levels of bioactive silicate glass. Microspheres contain (a) 2%, (b) 5%. (c) 10%, (d) 20%, and (e) 40% BSG by polymer weight. Arrows show the locations of BSG agglomerations on the surfaces of the microspheres. When present in a sphere-to-sphere bond region, BSG agglomerations decrease the surface area available for sintering—weakening sphere-to-sphere junctions. Microspheres with more BSG agglomerations result in greater bond occlusion. Ovals encircle examples of microsphere bonds where no BSG interference is visible. Again, optimization of BSG content entailed maximizing BSG content for bioactivity while minimizing large BSG agglomerations; 10% BSG content was considered optimal.

Dispersion of BSG within the composite was visualized using microCT (FIGS. 4(a)-4(c)).

Example 2. Mechanical Testing and Porosity

Figure 5:
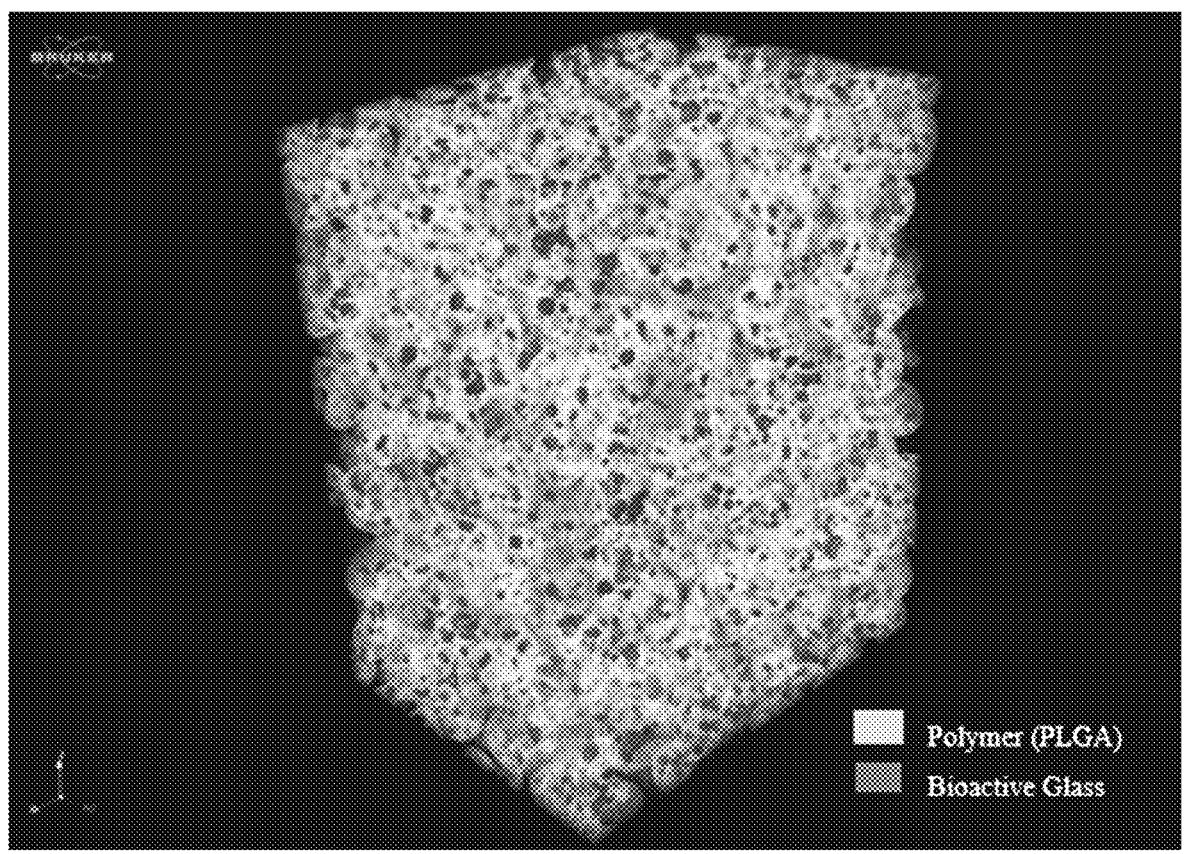
FIG. 5: Micro-CT image of optimized 10% BSG composite microsphere scaffold. The location of BSG within the scaffold is indicated in red. BSG is homogenously dispersed throughout the scaffold.

Distribution of BSG within the composite was visualized using a Skyscan 1172 microCT (FIG. 5). BSG was dispersed homogeneously throughout the scaffold.

Porosities of pure PLGA and composite scaffolds were approximated using Quantum GX microCT. In the composite scaffold, interconnected pore space accounted for about 26.6% of the total scaffold volume. Pure PLGA scaffold interconnected pores accounted for about 37.7% of the total scaffold volume.

Compression testing of both scaffold types revealed a triphasic stress vs strain relationship [35]. An initial phase of elastic deformation was followed by a phase of inelastic compression—where applied stress remained nearly constant during continued deformation. No failure point was reached; instead, once the scaffolds' pores collapsed in the inelastic phase, increased stress was required for further deformation. This final region of increasing stress characterized a third phase in the stress vs. strain curve which mimics that of trabecular bone. As trabeculae collapse during compression, pore spaces in the bone are filled—much like the pores collapsing in our microsphere scaffolds [35]. Additionally, the elastic modulus for each scaffold type was in the range of trabecular bone (20-900 MPa) [15, 35]. Still, elastic modulus was lower for the composite scaffold with 342±42 MPa and 525±68 MPa for composite and pure PLGA, respectively (one outlier was detected and removed for composite scaffolds). As discussed earlier, the presence of BSG agglomerations on the composite microspheres' surfaces may obstruct sphere-to-sphere contact and sintering. Weakened bonds allowed more deformation per unit of stress and diminished the composite scaffolds' elastic modulus.

Example 3. Biomimetic Studies

Scaffolds were retrieved from mSBF after one and two weeks, and their surfaces were examined with SEM and EDS to discern the deposited mineral structure and composition (FIGS. 6(a)-6(h) and FIGS. 7(a)-7(d)). Reaction of SBF or mSBF with a material can provide a prediction of that material's bioactivity—where acquisition of a calcium phosphate layer indicates the material may bond to native bone in a defect site.

Figures 6A, 6B, 6C, 6D, 6E, 6F, 6G, 6H:
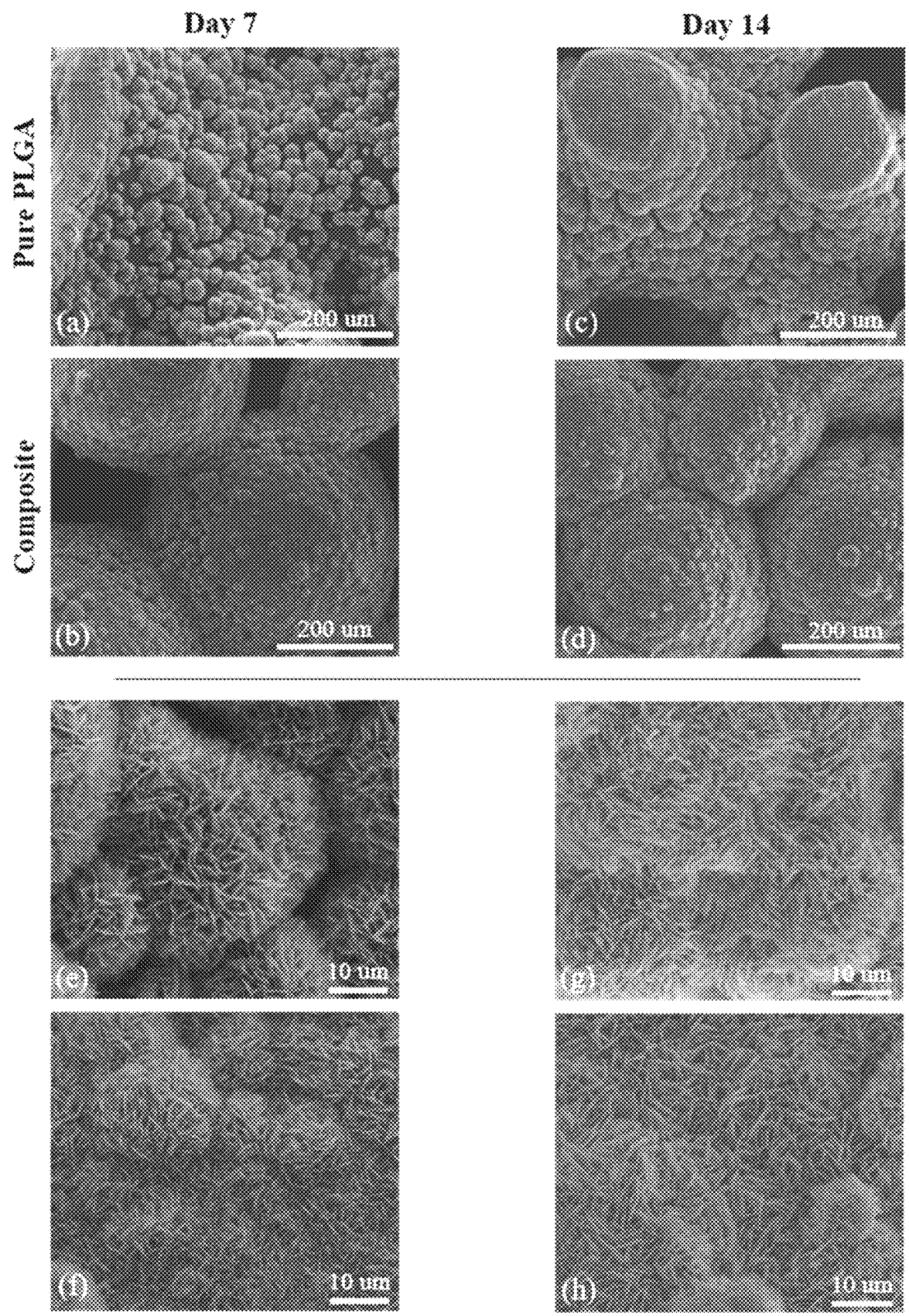
FIGS. 6(a)-6(h): SEM micrographs examined apatite morphology on scaffolds submerged in modified simulated body fluid (mSBF) for 7 (a,b) and 14 (c,d) days. Pure PLGA scaffolds (a,c) and composite scaffolds (b,d) initially formed 10-50 μm nucleation clusters at day 7; these covered the entire scaffold surface by day 14.
Figures 7A, 7B, 7C, 7D:
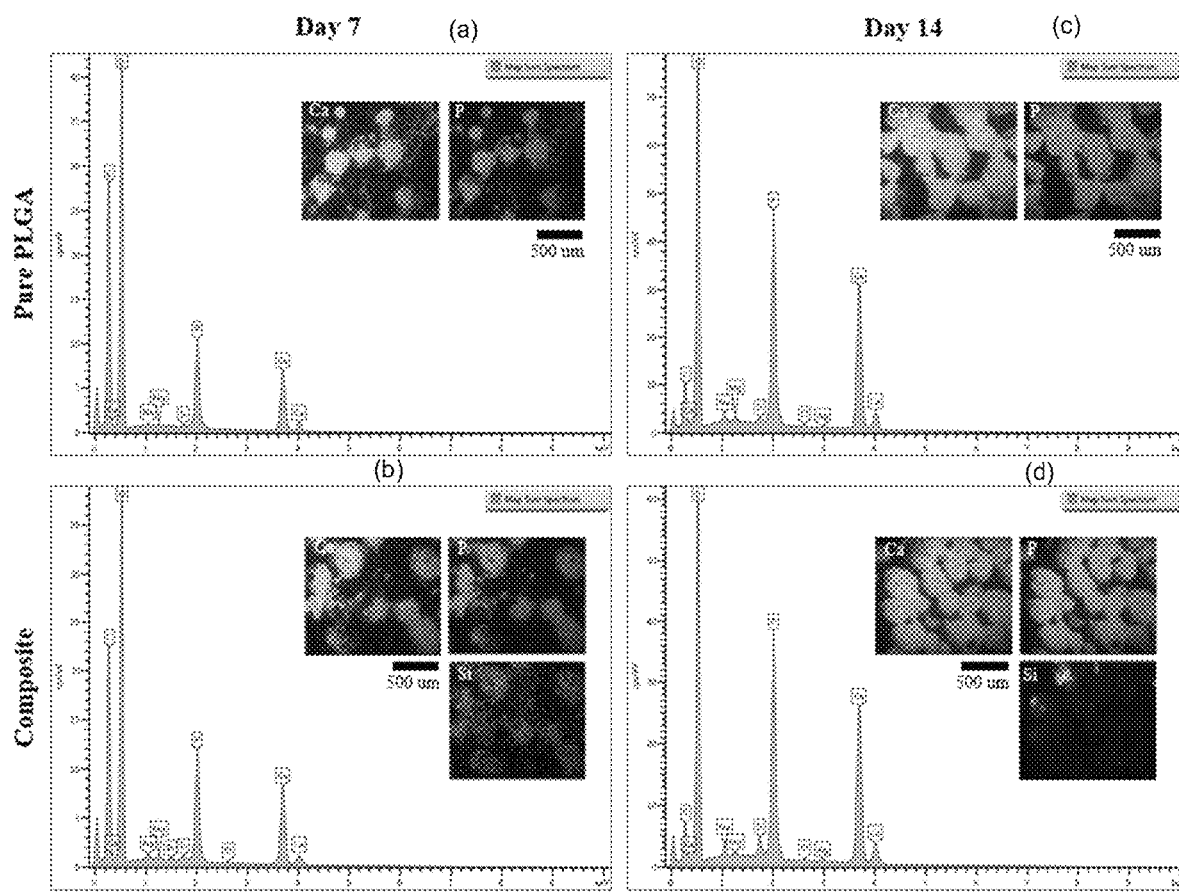

Mineral nucleation, initially forming 10-50 μm clusters at day 7 (FIGS. 6(a)-6(b)), covered both pure PLGA and composite scaffold surfaces by day 14 (FIGS. 6(c) and 6(d)). Mineral morphology appeared as randomly oriented plate-like structures, 3-5 μm wide (FIGS. 6(e)-6(f)). EDS mapping confirmed the layer to consist primarily of calcium phosphate with a 1.5-1.6 calcium to phosphorous ratio (FIGS. 7(a)-7(d)) (Table 1). This ratio is close to that of hydroxyapatite (bone mineral) and tricalcium phosphate—1.67 and 1.5 respectively [36]. Although pure PLGA is not considered bioactive, it did acquire a mineral layer after submersion in mSBF for seven days. The mechanism for mineral deposition on PLGA is well-defined: hydrolyzed PLGA bonds expose hydroxyl and carboxyl functional, these partially negative functional groups attract calcium cations, which sequentially attract phosphate anions [37]. Many iterations of cation and anion deposition eventually produce visible mineralization on the polymer surface.

Early nucleation on the pure PLGA scaffold was preferential to regions of the scaffold surface that had contacted the mold during sintering. These regions had sharp edges and rough surfaces, in contrast to the smooth surfaces of the spheres, which served as nucleation points for mSBF mineralization. By day 14, mineralization in these regions formed massive clusters almost 200 μm in diameter. Composite scaffolds also mineralized on rough or sharp areas; however, by day 14 the entire scaffold was covered in a lawn of mineralization. Discernible clusters of mineralization were not larger than 100 μm in diameter—suggesting that mineralization occurred more homogeneously than on pure PLGA. Monoliths of phytic acid-derived glasses of similar compositions were tested in SBF by Li et al. [38]. XRD analysis of a 35% CaO, 54% SiO2, 11% P2O5 sample exhibited Bragg peaks characteristic of hydroxyapatite after 14 days of treatment in SBF [38].

Example 4. hMSC Viability and Scaffold Coverage

Figures 8A, 8B, 8C, 8D, 8E, 8F, 8G, 8H:
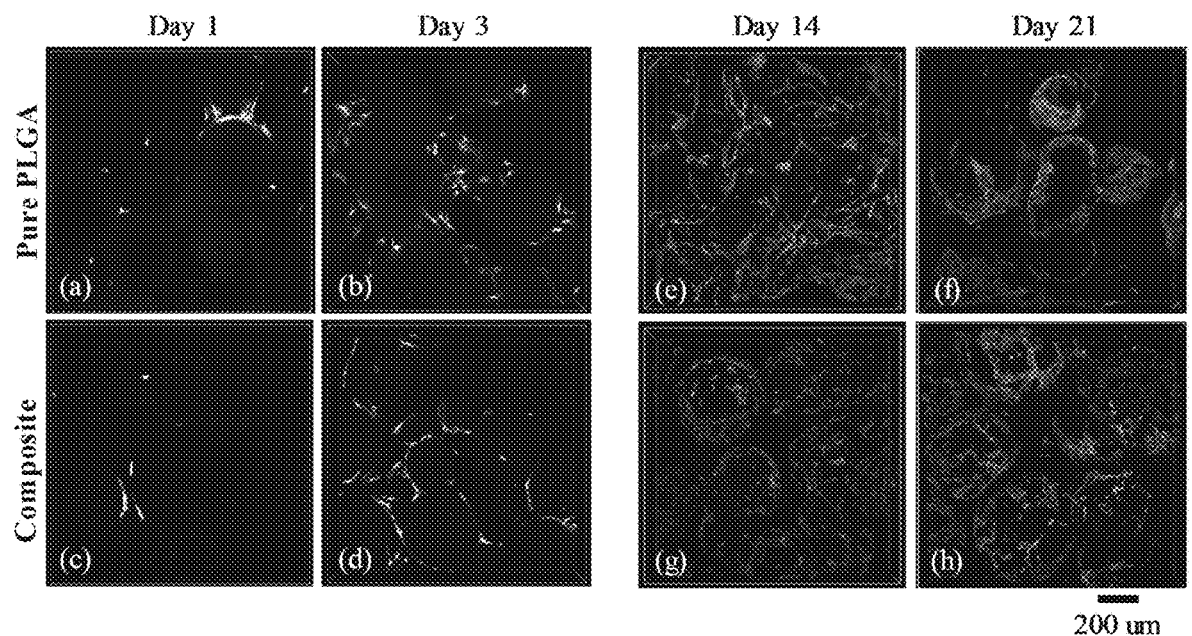
Figures 9A, 9B, 9C, 9D:
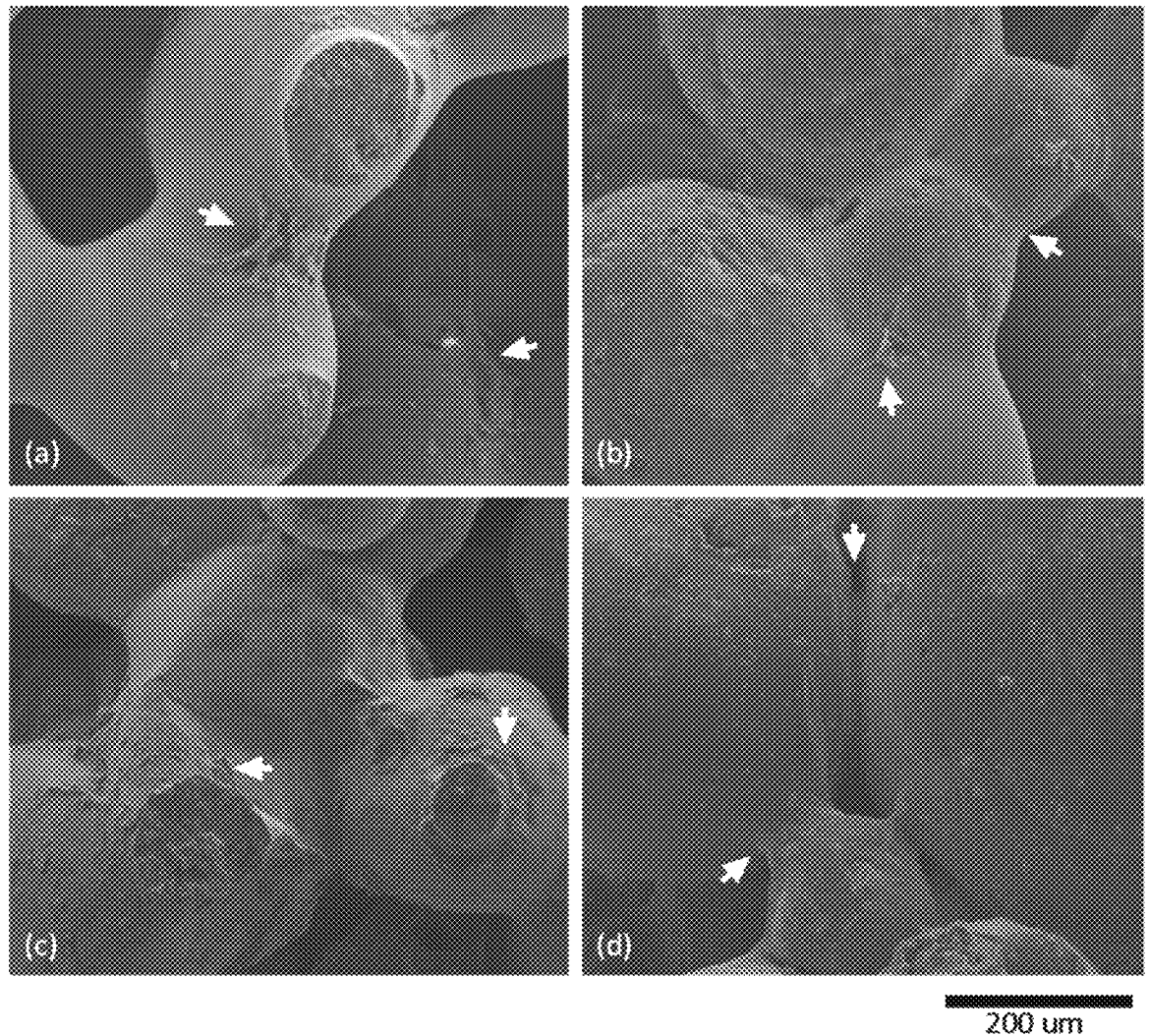

On day one, a live-dead fluorescent assay examined viable cells within 100 μm thick sections of each scaffold type (FIGS. 8(a) and 8(c)). Live hMSCs fluoresced green and elongated morphology; dead cells had a small, round morphology and fluoresced red. There were no apparent differences in cell viability between pure PLGA and composite scaffolds. The hMSCs were attached to the scaffolds and began to bridge gaps between adjacent microspheres. At day three, viability was evaluated in 300 μm thick sections of the scaffolds (FIGS. 8(b) and 8(d)); again, there were no apparent viability or morphology differences between pure PLGA and composite scaffolds; both supported hMSC attachment and viability.

At days 14 and 21, the cells were more confluent than at earlier time points (FIGS. 8(e)-8(h)). Cells at day 14 still had an elongated morphology; however, as cell-to-cell contact increased, individual cytoskeletons could not be discerned. By day 21, extensive scaffold coverage made it possible for microsphere shapes to be discerned. This is especially apparent on pure PLGA scaffolds at day 21 (FIG. 8(f)).

Scanning electron micrographs also indicated extensive scaffold coverage at days 14 and 21 (FIGS. 9(a)-9(d)). By day 14, the hMSCs had covered the topmost layer of the scaffold—observed by changes in scaffold topography and cell bridging between adjacent microspheres. Without cell coverage, pure PLGA scaffold surfaces appeared smooth with sharply defined bond regions. Composite scaffolds appeared similarly except for occasional BSG surface agglomerations. By two and three weeks of cell culture, surfaces and bond regions were masked with cells and ECM components—creating rough, irregular surface features and concealing bond areas. Where deeper scaffold layers could be seen, cell infiltration beyond the topmost layer was apparent.

Example 5. hMSC Proliferation

Proliferation was quantified with a PicoGreen assay as DNA concentration per mL. On average, DNA concentration in sample lysates was higher for pure PLGA scaffolds than composite at days 7, 14, and 21. This difference was statistically significant at days 14 ($p<0.01$) and 21 ($p<0.05$). Since live/dead assays showed no differences in cell viability between scaffold types, lowered DNA concentration on composite scaffolds was not attributed to cell death. Instead, hMSC progression towards the osteoblast lineage was examined as a potential cause. As hMSCs begin to differentiate, cell proliferation slows and eventually ceases [39]. ALP activity and ECM calcification were measured to determine the extent of osteogenic differentiation on each scaffold type.
3.3.3 hMSC Osteogenic Differentiation ALP activity is detectable in early osteogenic differentiation, and ALP expression increases until osteoblasts begin to embed in bone mineral—becoming osteocytes [39]. ALP activity was assayed to quantify osteogenic differentiation and was reported on a per cell basis by normalizing absorbance to DNA concentration. On average, normalized ALP activity was greater on the composite scaffolds at all measured time points, but these differences were statistically significant only at days 7 and 14 (FIG. 10(a)). Presence of ALP activity at day 7 signals that osteogenic differentiation is already underway. Greater ALP activity per cell on composite scaffolds is evidence that the novel BSG has prompted hMSCs further along the path of differentiation.

Calcification of cell-deposited ECM is a sign of late-stage differentiation—occurring after proliferation and initial ECM deposition [39]. Alizarin red stain adhered to calcified ECM and was qualitatively observed for homogeneity and intensity (FIG. 10(c)). Both scaffold types appeared to have similar staining intensity, but it appeared less homogenous on the pure PLGA scaffolds. Greater opacity in the composite material may have obscured staining below the surface layer of microspheres. Inclusion of BSG in the polymer imparted opaqueness to the composite—whereas pure PLGA scaffolds were translucent.

To obtain a true comparison of scaffold mineralization, the quantity of adhered alizarin stain was assessed. Scaffold stains were dissolved in 10% CPC, and the resultant solutions measured for absorbance (FIG. 10(b)). Absorbance was normalized to DNA concentration to report ECM calcification on a per cell basis. At day 14, cell-deposited mineralization was low, but pure PLGA scaffolds contained slightly more calcified matrix per cell versus composite ($p<0.05$). At day 21, cells on the composite scaffold had produced substantially more calcified matrix than those on pure PLGA ($p<0.01$). Matrix deposition with low mineralization at day 14 aligns with post-proliferative, early osteogenic differentiation. By day 21, cells on the composite scaffolds may have entered late-stage differentiation—marked by extensive ECM calcification.

REFERENCES

[1] A. S. Greenwald, S. D. Boden, V. M. Goldberg, Y. Khan, C. T. Laurencin, R. N. Rosier, Bone-graft substitutes: facts, fictions, and applications, J. Bone Joint Surg. Am. 83-A Suppl 2 Pt 2 (2001) 98-103.

[2] Q. Lv, M. Deng, B. D. Ulery, L. S. Nair, C. T. Laurencin, Nano-ceramic composite scaffolds for bioreactor-based bone engineering, Clin. Orthop. Relat. R. 471(8) (2013) 2422-33.

[3] A. R. Amini, C. T. Laurencin, S. P. Nukavarapu, Bone tissue engineering: recent advances and challenges, Crit. Rev. Biomed. Eng. 40(5) (2012) 363-408.

[4] C. Delloye, O. Cornu, V. Druez, O. Barbier, Bone allografts: What they can offer and what they cannot, J. Bone Joint Surg. Br. 89(5) (2007) 574-9.

[5] E. K. Cushnie, B. D. Ulery, S. J. Nelson, M. Deng, S. Sethuraman, S. B. Doty, K. W. Lo, Y. M. Khan, C. T. Laurencin, Simple signaling molecules for inductive bone regenerative engineering, PLoS One 9(7) (2014) e101627.

[6] R. G. Geesink, N. H. Hoefnagels, S. K. Bulstra, Osteogenic activity of OP-1 bone morphogenetic protein (BMP-7) in a human fibular defect, J. Bone Joint Surg. Br. 81(4) (1999) 710-8.

[7] N. F. Chen, Z. A. Smith, E. Stiner, S. Armin, H. Sheikh, L. T. Khoo, Symptomatic ectopic bone formation after off-label use of recombinant human bone morphogenetic protein-2 in transforaminal lumbar interbody fusion, J. Neurosurg. Spine 12(1) (2010) 40-6.

[8] M. R. Urist, Bone: formation by autoinduction, Science 150(3698) (1965) 893-899.

[9] A. Nauth, J. Ristiniemi, M. D. McKee, E. H. Schemitsch, Bone morphogenetic proteins in open fractures: past, present, and future, Injury 40 Suppl 3 (2009) S27-31.

[10] F. Wegman, R. E. Geuze, Y. J. van der Helm, F. Cumhur Öner, W. J. Dhert, J. Alblas, Gene delivery of bone morphogenetic protein-2 plasmid DNA promotes bone formation in a large animal model, J. Tissue Eng. Regen. Med. 8(10) (2014) 763-70.

[11] M. Deng, E. K. Cushnie, Q. Lv, C. T. Laurencin, Poly(lactide-co-glycolide)-Hydroxyapatite Composites: The Development of Osteoinductive Scaffolds for Bone Regenerative Engineering Mater. Res. Soc. Symp. P., Cambridge University Press, 2012.

[12] M. Deng, R. James, C. T. Laurencin, S. G. Kumbar, Nanostructured polymeric scaffolds for orthopaedic regenerative engineering, IEEE T. Nanobiosci. 11(1) (2012) 3-14.

[13] C. Laurencin, M. Attawia, L. Lu, M. Borden, H. Lu, W. Gorum, J. Lieberman, Poly (lactide-co-glycolide)/hydroxyapatite delivery of BMP-2-producing cells: a regional gene therapy approach to bone regeneration, Biomaterials 22(11) (2001) 1271-1277.

[14] A. M. Wojtowicz, K. L. Templeman, D. W. Hutmacher, R. E. Guldberg, A. J. García, Runx2 overexpression in bone marrow stromal cells accelerates bone formation in critical-sized femoral defects, Tissue Eng. Pt. A 16(9) (2010) 2795-808.

[15] N. Narayanan, C. Jiang, G. Uzunalli, S. K. Thankappan, C. T. Laurencin, M. Deng, Polymeric Electrospinning for Musculoskeletal Regenerative Engineering, Regen. Eng. Transl. Med. 2(2) (2016) 69-84.

[16] M. J. Dalby, N. Gadegaard, R. Tare, A. Andar, M. O. Riehle, P. Herzyk, C. D. Wilkinson, R. O. Oreffo, The control of human mesenchymal cell differentiation using nanoscale symmetry and disorder, Nat. Mater. 6(12) (2007) 997-1003.

[17] J. L. Brown, M. S. Peach, L. S. Nair, S. G. Kumbar, C. T. Laurencin, Composite scaffolds: bridging nanofiber and microsphere architectures to improve bioactivity of mechanically competent constructs, J. Biomed. Mater. Res. A 95(4) (2010) 1150-8.

[18] M. Alcaide, P. Portolés, A. López-Noriega, D. Arcos, M. Vallet-Regí, M. T. Portolés, Interaction of an ordered mesoporous bioactive glass with osteoblasts, fibroblasts and lymphocytes, demonstrating its biocompatibility as a potential bone graft material, Acta Biomater. 6(3) (2010) 892-9.

[19] P. Müller, U. Bulnheim, A. Diener, F. Lüthen, M. Teller, E. D. Klinkenberg, H. G. Neumann, B. Nebe, A. Liebold, G. Steinhoff, Calcium phosphate surfaces promote osteogenic differentiation of mesenchymal stem cells, J. Cell. Mol. Med. 12(1) (2008) 281-291.

[20] H. Yuan, H. Fernandes, P. Habibovic, J. de Boer, A. M. Barradas, A. de Ruiter, W. R. Walsh, C. A. van Blitterswijk, J. D. de Bruijn, Osteoinductive ceramics as a synthetic alternative to autologous bone grafting, P. Natl. Acad. Sci. USA 107(31) (2010) 13614-9.

[21] A. K. Gaharwar, S. M. Mihaila, A. Swami, A. Patel, S. Sant, R. L. Reis, A. P. Marques, M. E. Gomes, A. Khademhosseini, Bioactive silicate nanoplatelets for osteogenic differentiation of human mesenchymal stem cells, Adv. Mater. 25(24) (2013) 3329-36.

[22] Y. C. Chai, S. J. Roberts, J. Schrooten, F. P. Luyten, Probing the osteoinductive effect of calcium phosphate by using an in vitro biomimetic model, Tissue Eng. Pt. A 17(7-8) (2011) 1083-97.

[23] R. Z. LeGeros, Calcium phosphate-based osteoinductive materials, Chem. Rev. 108(11) (2008) 4742-53.

[24] L. L. Hench, R. J. Splinter, W. C. Allen, T. K. Greenlee, Bonding Mechanisms at the Interface of Ceramic Prosthetic Materials, J. Biomed. Mater. Res. Symp. 5(6) (1971) 25.

[25] A. R. Amini, D. J. Adams, C. T. Laurencin, S. P. Nukavarapu, Optimally porous and biomechanically compatible scaffolds for large-area bone regeneration, Tissue Eng. Pt. A 18(13-14) (2012) 1376-88.

[26] C. Wang, H. Shen, Y. Tian, Y. Xie, A. Li, L. Ji, Z. Niu, D. Wu, D. Qiu, Bioactive nanoparticle-gelatin composite scaffold with mechanical performance comparable to cancellous bones, ACS Appl. Mater. Inter. 6(15) (2014) 13061-13068.

[27] T. Jiang, W. I. Abdel-Fattah, C. T. Laurencin, In vitro evaluation of chitosan/poly(lactic acid-glycolic acid) sintered microsphere scaffolds for bone tissue engineering, Biomaterials 27(28) (2006) 4894-903.

[28] C. Xu, P. Su, X. Chen, Y. Meng, W. Yu, A. P. Xiang, Y. Wang, Biocompatibility and osteogenesis of biomimetic Bioglass-Collagen-Phosphatidylserine composite scaffolds for bone tissue engineering, Biomaterials 32(4) (2011) 1051-8.

[29] K. A. Athanasiou, C. Zhu, D. R. Lanctot, C. M. Agrawal, X. Wang, Fundamentals of biomechanics in tissue engineering of bone, Tissue Eng. 6(4) (2000) 361-81.

[30] T. Kokubo, H. Takadama, How useful is SBF in predicting in vivo bone bioactivity?, Biomaterials 27(15) (2006) 2907-15.

[31] G. Hou, F. Zhou, Y. Guo, Z. Yang, A. Li, C. Wang, D. Qiu, In vivo study of a bioactive nanoparticle-gelatin composite scaffold for bone defect repair in rabbits, J Mater Sci Mater Med 28(11) (2017) 181.

[32] J. Liuyun, X. Chengdong, C. Dongliang, J. Lixin, Effect of n-HA with different surface-modified on the properties of n-HA/PLGA composite, Appl. Surf. Sci. 259 (2012) 72-78.

[33] Z. Hong, P. Zhang, C. He, X. Qiu, A. Liu, L. Chen, X. Chen, X. Jing, Nano-composite of poly(L-lactide) and surface grafted hydroxyapatite: mechanical properties and biocompatibility, Biomaterials 26(32) (2005) 6296-304.

[34] Q. Zhang, V. N. Mochalin, I. Neitzel, I. Y. Knoke, J. Han, C. A. Klug, J. G. Zhou, P. I. Lelkes, Y. Gogotsi, Fluorescent PLLA-nanodiamond composites for bone tissue engineering, Biomaterials 32(1) (2011) 87-94.

[35] T. M. Keaveny, W. C. Hayes, Mechanical properties of cortical and trabecular bone, Bone 7 (1993) 285-344.

[36] Q. Lv, K. W. H. Lo, L. S. Nair, C. T. Laurencin, Calcium-Phosphate-Based Ceramics for Biomedical Applications in: A. J. Domb, N. Kumar, A. Ezra (Eds.), Biodegradable Polymers in Clinical Use and Clinical Development, John Wiley & Sons, Inc. 2011.

[37] W. L. Murphy, D. J. Mooney, Bioinspired growth of crystalline carbonate apatite on biodegradable polymer substrata, J. Am. Chem. Soc. 124(9) (2002) 1910-7.

[38] A. Li, D. Qiu, Phytic acid derived bioactive CaO—P2O5-SiO2 gel-glasses, J. Mater. Sci. Mater. M. 22(12) (2011) 2685-91.

[39] J. E. Aubin, Mesenchymal Stem Cells and Osteoblast Differentiation, in: J. P. Bilezikian, L. G. Raisz, T. J. Martin (Eds.), Principles of Bone Biology, Academic Press. Inc. 2008, pp. 85-107.

The invention claimed is:

1. A composite scaffold material of microspheres comprising a biodegradable polymer and a bioactive silicate glass (BSG), wherein said BSG comprises $SiO_2$, $P_2O_5$, and CaO, and $Na_2O$ is absent in said BSG, and wherein said BSG is dispersed in said biodegradable polymer to form a microsphere with a diameter from 250 μm to 500 μm, and wherein pores of said porous biocompatible scaffold material account for about 20-40% of the scaffold total volume with sufficient pore sizes of at least 100 μm to allow for seeding and growth of cells.

2. The composite scaffold material of microspheres according to claim 1, wherein the biodegradable polymer comprises poly(glycolic acid) (PGA), poly(lactic acid) (PLA), poly(lactic-co-glycolic acid) (PLGA), polycaprolactone (PCL), poly(propylene fumarate), collagen, polyphosphazenes, polyanhydrides, poly(amino acids), polyhydroxyalkanoates, polyethylene glycol (PEG), polydioxanone (PDO), a polysaccharide, or a combination of two or more said biodegradable polymers.

3. The composite scaffold material of microspheres according to claim 1, wherein the BSG accounts for 2%-30% by weight of the composite.

4. The composite scaffold material of microspheres according to claim 3, wherein the BSG comprises about 9% by weight of the composite.

5. The composite scaffold material of microspheres according to claim 1, wherein the BSG comprises about 6~80 mol % $SiO_2$.

6. The composite scaffold material of microspheres according to claim 1, wherein the BSG comprises about 0~70 mol % $P_2O_5$.

7. The composite scaffold material of microspheres according to claim 1, wherein the BSG comprises about 15~85 mol % CaO.

8. The composite scaffold material of microspheres according to claim 1, wherein the BSG comprises about 10.8 mol % $P_2O_5$, about 54.2 mol % $SiO_2$, and about 35.0 mol % CaO.

9. The composite scaffold material of claim 1, wherein the scaffold material has mechanical properties compatible with native bone with a compressive modulus value in the range of 300-600 MPa.

10. A method of fabricating a composite scaffold material of claim 1, comprising the steps of:
   a. dissolving a biodegradable polymer selected from the group consisting of poly(glycolic acid) (PGA), poly (lactic acid) (PLA), poly(lactic-co-glycolic acid) (PLGA), polycaprolactone (PCL), poly(propylene fumarate), collagen, polyphosphazenes, polyanhydrides, poly(amino acids), polyhydroxyalkanoates, polyethylene glycol (PEG), polydioxanone (PDO), a polysaccharide, or a combination of any two or more said biodegradable polymers in a solvent to form a polymer solution;
   b. adding BSG powder, wherein said BSG powder comprises $SiO_2$, $P_2O_5$, and CaO, and $Na_2O$ is absent in said BSG, into the polymer solution to afford a polymer/glass suspension solution; and
   c. pouring the polymer/glass suspension solution into a polyvinyl alcohol (PVA) solution to afford a mixture and removing the solvent from the mixture under stirring followed by drying and sintering temperature to afford the composite scaffold material of microspheres.

11. The method of claim 10, wherein the BSG powder is incorporated said polymer/glass suspension solution via sonication, vortex mixing, or a combination thereof.

12. The method of claim 10, wherein the solvent is an organic or an inorganic compatible solvent.

13. A method of effecting bone repair comprising contacting an area affected by a bone defect with the composite scaffold material of claim 1.

14. The method of claim 13, wherein the composite scaffold material further comprises a bioactive agent selected from the group consisting of bone morphogenic proteins (BMPs), vascular endothelial growth factor (VEGF), connective tissue growth factor (CTGF), osteoprotegerin, growth differentiation factors (GDFs), cartilage-derived morphogenic proteins (CDMPs), LIM mineralization proteins (LMPs), transforming growth factor β (TGFβ), antibiotics, immunosuppressive agents, and any combinations thereof.

15. The method of claim 13, wherein the composite scaffold material further contains host-derived cells comprising mesenchymal stem cells, osteoprogenitors, pre-osteoblasts, osteoblasts, or a combination thereof.

* * * * *